United States Patent [19]
Okada et al.

[11] Patent Number: 5,661,537
[45] Date of Patent: Aug. 26, 1997

[54] OPHTHALMIC AUXILIARY INSTRUMENT AND OPHTHALMIC SYSTEM USING THE SAME INSTRUMENT

[75] Inventors: Masaru Okada; Masanobu Kaneko, both of Yokohama, Japan

[73] Assignee: Nikon Corporation, Tokyo, Japan

[21] Appl. No.: 616,100

[22] Filed: Mar. 14, 1996

[30] Foreign Application Priority Data

Mar. 16, 1995 [JP] Japan .................................. 7-057604

[51] Int. Cl.$^6$ .................................. G02C 1/00; A61B 3/10
[52] U.S. Cl. .................................. 351/158; 351/216
[58] Field of Search .................................. 351/205, 209, 351/216, 210, 214, 245, 200, 158

[56] References Cited

U.S. PATENT DOCUMENTS 2,622,473 12/1952 Littmann .................................. 351/216

FOREIGN PATENT DOCUMENTS

6-50601  7/1994  Japan .

*Primary Examiner*—Huy Mai
*Attorney, Agent, or Firm*—Shapiro and Shapiro

[57] ABSTRACT

An auxiliary instrument for observing a fundus of eye, comprises an ophthalmic lens for forming an image of light beam reflected by the fundus of an examined eye, a lens holding member for holding the ophthalmic lens, a frame mounted with the lens holding member and put on the head or a part of the face of an examinee so that the ophthalmic lens is located in front of the examined eye of the examinee, and an inclination mechanism, provided between the lens holding member and the frame, for inclining an optical axis of the ophthalmic lens at a predetermined angle to an optical axis of the examined eye.

9 Claims, 7 Drawing Sheets

OPHTHALMIC AUXILIARY INSTRUMENT AND OPHTHALMIC SYSTEM USING THE SAME INSTRUMENT

BACKGROUND OF THE INVENTION

1. Field of the Invention

The present invention relates generally to an ophthalmic auxiliary instrument and, more particularly, to a fundus of eye observation auxiliary instrument for holding a non-contact type aspherical inverted image lens for observing a fundus of eye which instrument is used with a slit-lamp microscope. The present invention also relates to an ophthalmic system for observing a fundus of eye or a cornea by use of the same auxiliary instrument.

2. Related Background Art

A prior art will be explained with reference to FIGS. 7 to 10.

Figure 7:
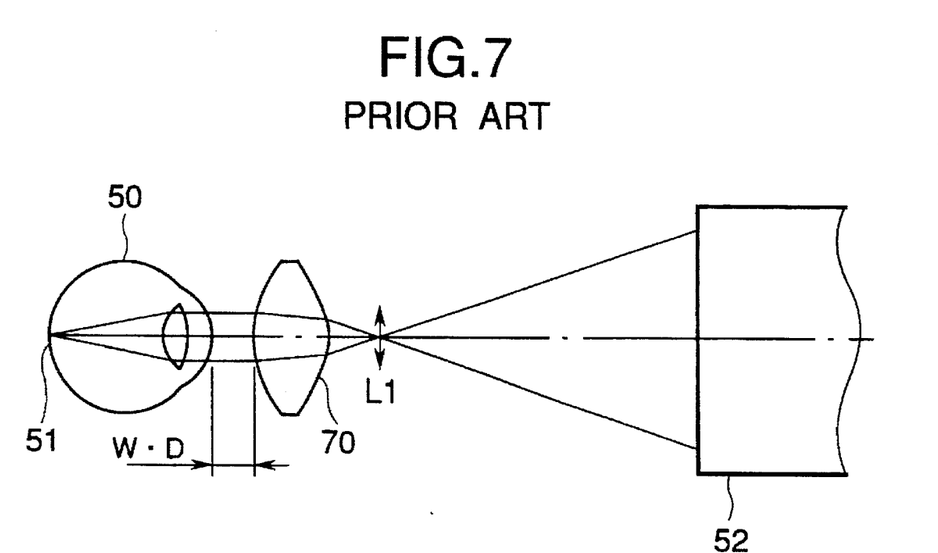
FIG. 7 is an explanatory view showing the principle for observing a fundus of eye by use of an aspherical inverted image lens.
Figure 8:
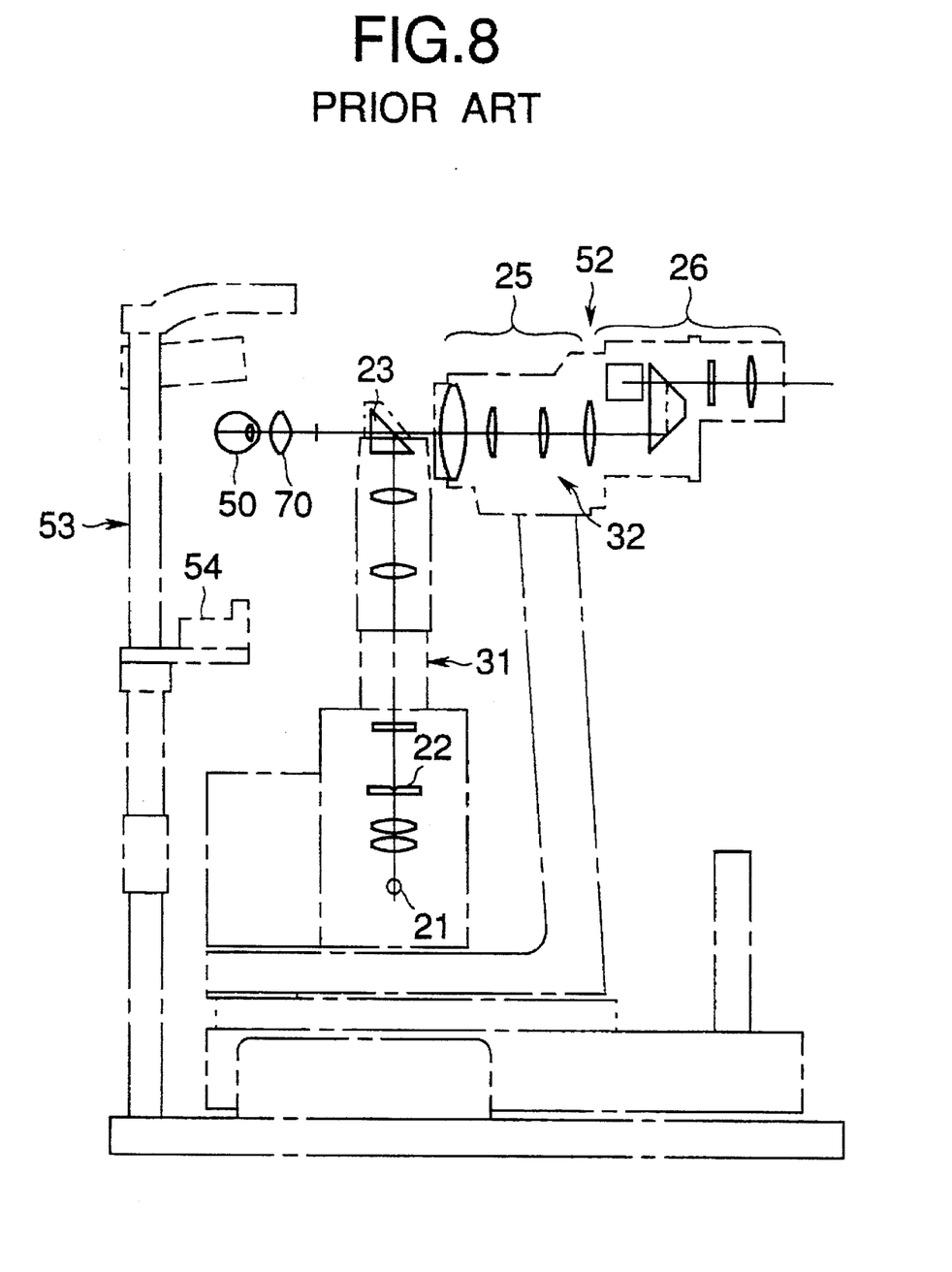
FIG. 8 is an explanatory view schematically showing a construction of a slit-lamp microscope according to prior art.

Referring to FIG. 7, the numeral 50 designates an examined eye (eyeball), 51 represents a fundus of eye, 70 denotes an aspherical inverted image lens for observing the fundus of eye, and 52 indicates the side of an objective lens of a slit-lamp microscope. FIG. 8 illustrates how the fundus of eye of the examined eye is observed through the aspherical inverted image lens 70 by using the slit-lamp microscope 52 in combination.

The slit-lamp microscope 52 is, as illustrated in FIG. 8, constructed of an illumination optical system 31 and an observation optical system 32. The illumination optical system 31 has a halogen lamp 21 and a slit stop 22 for forming a slit light beam from the light beams emitted by the halogen lamp 21.

Normally, the slit-lamp microscope 52 forms an image of the light beam emerging from the slit stop 22 on the cornea of an examined eye 50 or a crystal lens, and a lesion of a front eye part (ranging from the cornea to the crystal lens) is observed with the aid of the slit beam.

The slit beam exiting the slit stop 22 is, after passing through respective lenses, deflected in its optical path by the prism 23. The deflected slit beam is, after traveling through the aspherical inverted image lens 70, image-formed on the fundus 51 of the examined eye 50. The reflected beam from the fundus of eye 51, as illustrated in FIG. 7, again passes through the aspherical inverted image lens 70 and is then image-formed in a focal position L1. The image of the fundus of eye is observed in enlargement by an eyepiece element 26 as well as by an objective element 25 of the observation optical system 32 of the slit-lamp microscope 52. The slit beam from the slit-lamp microscope 52 is short of a quantity of illumination light as an illumination light beam with which the fundus of eye is illuminated. For this reason, the slit beam from the slit-lamp microscope 52 is temporarily is image-formed in the focal position L1, and the slit beam image-formed in the focal position L1 is then image-formed by the aspherical inverted image lens 50, thereby obtaining a light quantity enough for observing the fundus of eye.

As a matter of fact, when observing the image of the fundus of eye, the aspherical inverted image lens 70 is held with a hand and moved to a position in front of the examined eye but spaced away a predetermined distance, i.e., a so-called W.D (Working Distance) therefrom, and, further, an optical axis of the examined eye 50 is made coincident with an optical axis of the aspherical inverted image lens 70. At this time, the examiner manipulates the slit-lamp microscope 52 with the other hand to make the optical axis of the slit-lamp microscope 52 coincident with the optical axis of the aspherical inverted image lens. Then, the eyepiece element 26 and the objective element 25 including the observation optical system 32 of the slit-lamp microscope 52 are moved in the optical-axis directions to adjust the focal point, and the image of the fundus of eye is observed. Thus, considerably laborious operations must be performed.

Figure 9:
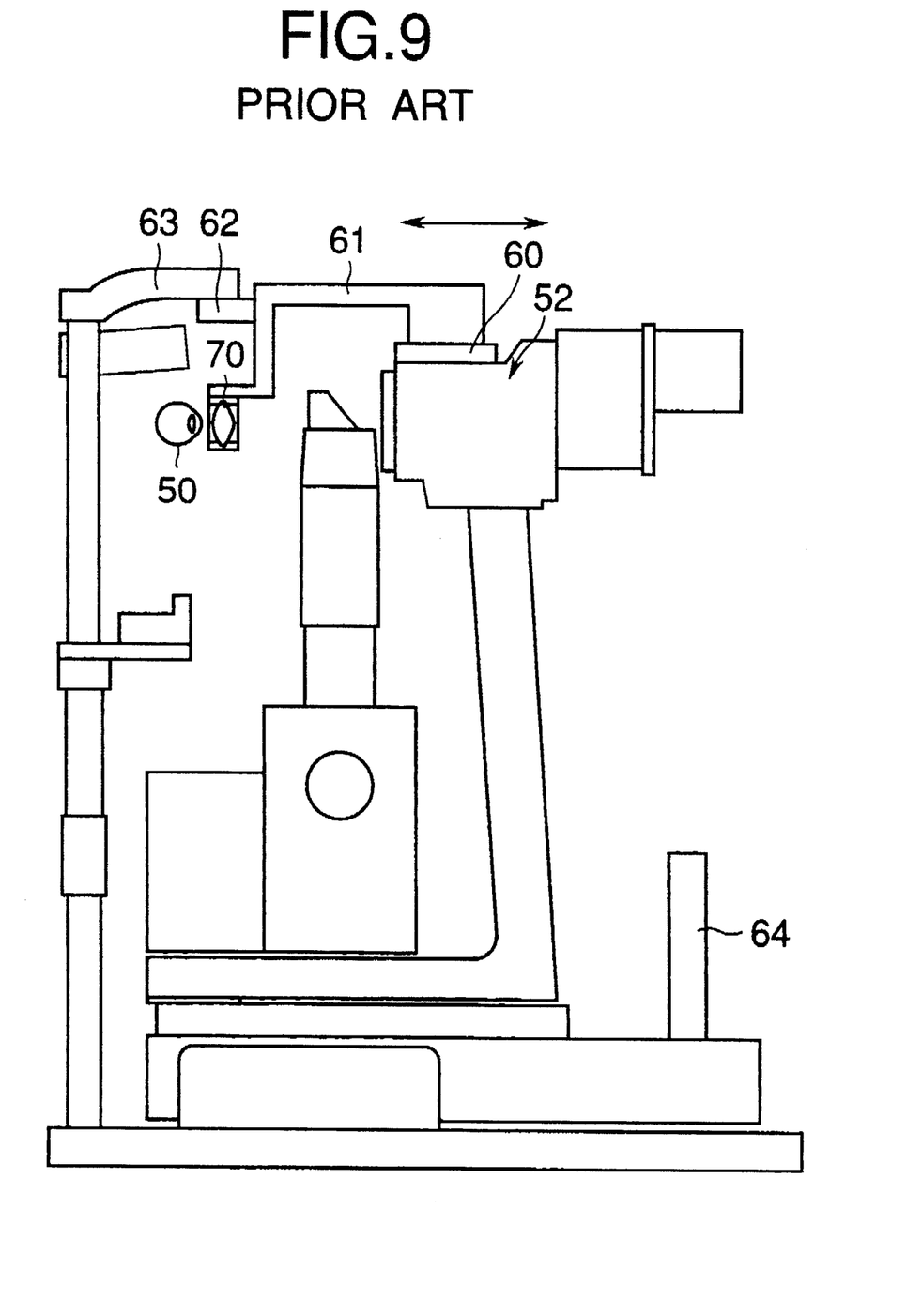
FIG. 9 is an explanatory view illustrating a state where the fundus of eye is observed by the slit-lamp microscope having a holder according to the prior art.

Then, facilitating such laborious operations as much as possible may involve the use of a variety of holders for holding the aspherical inverted image lens 70. FIG. 9 is a view illustrating one example of an external configuration of the slit-lamp microscope 52 equipped with the holder for the aspherical inverted image lens 70. A holder 61 is attached to the slit-lamp microscope 52 in this example. This holder 61 is so structured as to be movable in only a given range in the arrowed directions in FIG. 9 with respect to a mounting member 60 mounted to an upper portion of the slit-lamp microscope 52. Further, the holder 61 is always biased by spring action in the direction of the examined eye 50 and pushed against a W.D setting member 62 fitted to a forehead contact member 63.

The W.D setting member 62 is supported with respect to the forehead contact member 63 so that a pull-out quantity is adjustable on the side of the microscope 52. Accordingly, it is possible to adjust a distance between the aspherical inverted image lens 70 and the examined eye 50.

In this case, the optical axes of the slit-lamp microscope 52 and the aspherical inverted image lens 70 are made coincident beforehand by use of the holder 61, and hence the examiner makes it coincident with an optical axis of the examined eye 50 by use of a joy stick 64. Further, the slit-lamp microscope 52 is moved in the optical-axis directions (in the arrowed directions in FIG. 9), thus adjusting the focal point.

Figure 10:
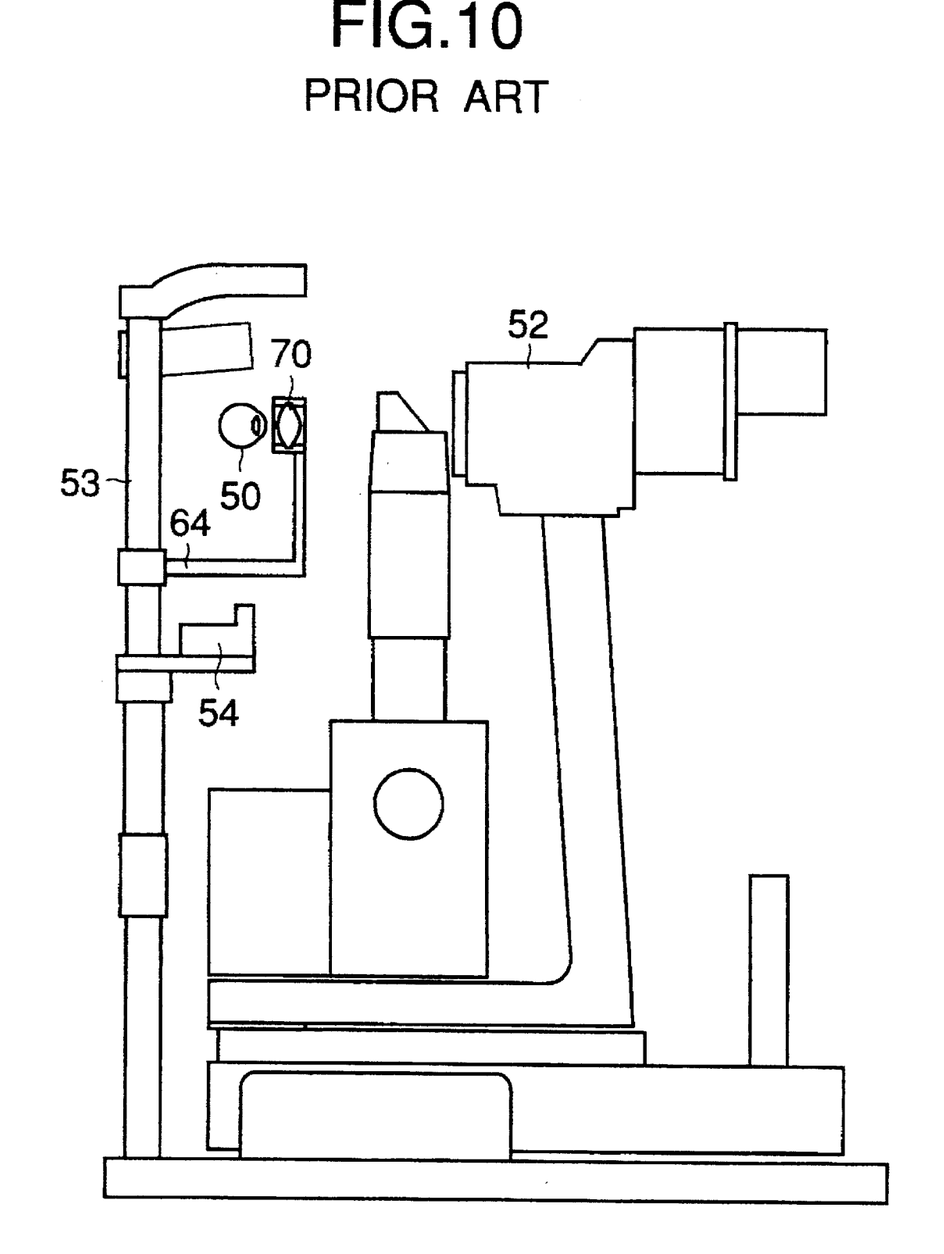
FIG. 10 is an explanatory view showing a state where the fundus of eye is observed by the slit-lamp microscope having the holder according to the prior art.

FIG. 10 shows a construction of the slit-lamp microscope 52 equipped with another type of holder. In the slit-lamp microscope 52 in this example, a holder 64 is attached to a chin sustainer rod 53. With the thus constructed holder 64, it is feasible to previously make the optical axis of the examined eye 50 coincident with the optical axis of the aspherical inverted image lens 70 and the optical axis of the slit-lamp microscope 52 unless the examinee moves the face from a chin sustainer 54 of the chin sustainer rod 53.

According to the construction of the slit-lamp microscope 52 including the above holder, the examiner has no necessity for holding the aspherical inverted image lens 70, and the operations are facilitated to some extent.

In the case of having the holders as shown in FIGS. 9 and 10, however, the optical axis of the aspherical inverted image lens 70 can be made easily coincident with the optical axis of the slit-lamp microscope 52. But, if the examinee moves the face even slightly, the optical axis of the slit-lamp microscope 52 deviates from the optical axis of the examined eye 50 (pupil), and besides W.D also changes. Hence, there arises a problem in which when observing the image of the fundus of eye, W.D has to be reset as well as readjusting the coincidence of the optical axes, and the laborious operations are required.

SUMMARY OF THE INVENTION

It is a primary object of the present invention, which was contrived to obviate such a problem inherent in the prior art, to provide an auxiliary instrument, capable of making easier the operation for observing an examined eye, for holding an ophthalmic lens.

It is another object of the present invention to provide an ophthalmic system using the same auxiliary instrument.

To accomplish the above objects, according to a first aspect of the present invention, an auxiliary instrument for observing a fundus of eye comprises an ophthalmic lens for forming an image of light beams reflected by the fundus of an examined eye, a lens holding member for holding the ophthalmic lens, a frame mounted with the lens holding member and put on the head or a part of the face of an examinee so that the ophthalmic lens is located in front of the examined eye of the examinee and an inclination mechanism, provided between the lens holding member and the frame, for inclining an optical axis of the ophthalmic lens at a predetermined angle to an optical axis of the examined eye.

According to a second aspect of the present invention, an ophthalmic system comprises a microscope for irradiating an examined eye with slit light beams, an ophthalmic lens for forming an image of the slit light beams on the examined eye and a frame, for holding the ophthalmic lens, put on the head of a part of the face of the examinee so that the ophthalmic lens is located in front of the examined eye and having an inclination mechanism for inclining an optical axis of the ophthalmic lens to an optical axis of the examined eye.

In the ophthalmic auxiliary instrument and the ophthalmic system using this auxiliary instrument, the lens holding member holding the ophthalmic lens is mounted in the frame, and the examinee wears this frame. The distance (W.D) of the ophthalmic lens from the pupil of the examinee and the optical-axis direction are thereby kept fixed at all times. Accordingly, even if the examinee moves the face, the examiner may make a readjustment so that the optical axis of the slit-lamp microscope coincides with the optical axis of the ophthalmic lens fixed to the frame. The examiner is able to observe the reflected image from the examined eye much easily than by the prior art.

Hence, the setting required for observing the reflected image from the examined eye is more facilitated, and the operations that have hitherto been laborious can be simplified.

BRIEF DESCRIPTION OF THE DRAWINGS

Other objects and advantages of the present invention will become apparent during the following discussion in conjunction with the accompanying drawings, in which.

DESCRIPTION OF THE PREFERRED EMBODIMENT

There will hereinafter be described one embodiment of an ophthalmic auxiliary instrument and an ophthalmic system using this auxiliary instrument to which the present invention is applied with reference to FIGS. 1 to 6.

The ophthalmic auxiliary instrument in this embodiment is used for observing a fundus of eye. The ophthalmic auxiliary instrument is constructed of an aspherical inverted image lens 10 for observing a fundus of eye, a holding frame 20 serving as a lens holding member for holding an aspherical inverted image lens and a spectacle frame 1 for fixing the aspherical inverted image lens 10 through the holding frame 20. Further, the ophthalmic system is used for observing the fundus of eye and includes the fundus of eye observation auxiliary instrument in this embodiment and a slit-lamp microscope 52.

Figure 1:
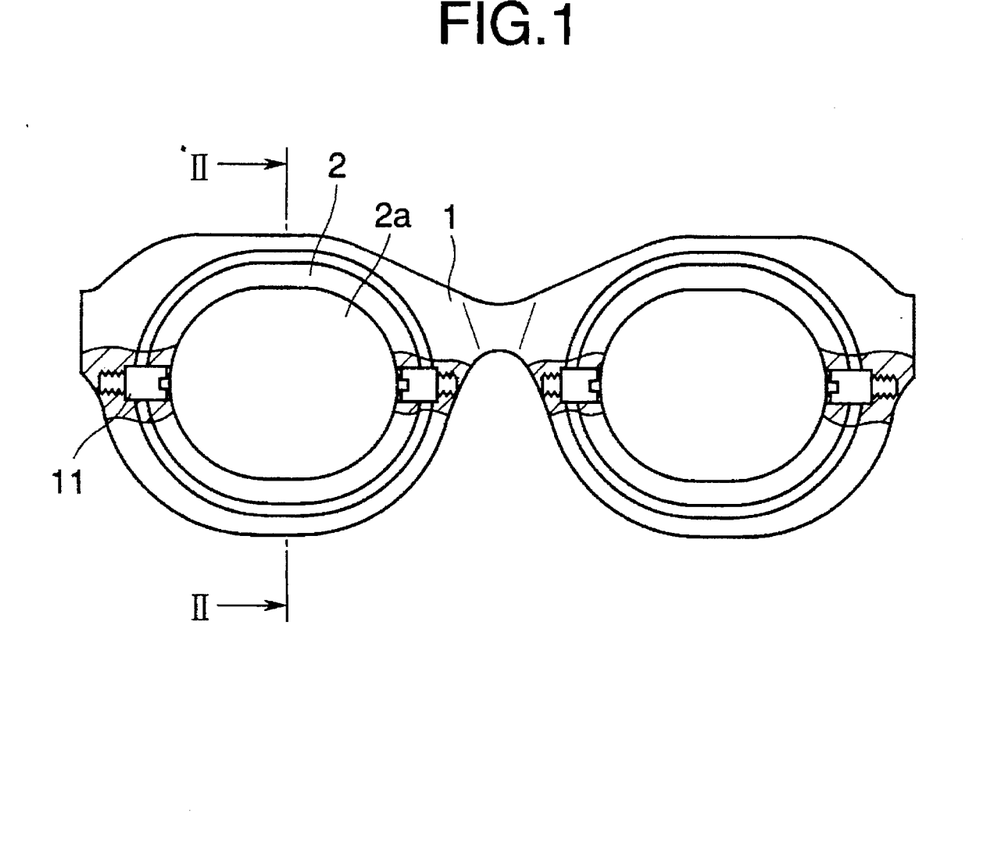
FIG. 1 is a front view illustrating one embodiment of an auxiliary instrument according to the present invention.

The auxiliary instrument in this embodiment has, as illustrated in, e.g., FIG. 1, the spectacle frame 1, holding plates 2 installed in two frames formed in the spectacle frame 1 and four pieces of screws 11 (provided right and left by twos) for fixing the holding plates to the spectacle frame 1.

The holding plates 2 are tabular members each smaller than an opening frame of the spectacle frame 1, assuming a similar shape and formed with an elongate hole 2a in the central portion thereof. The screws 11 are inserted in this holding plates 2 from inside toward outside in predetermined positions of side surfaces in the right-and-left directions (lateral directions) in the Figure, thus securing the holding plates 2 to the spectacle frame 1 with the screws 11. This holding plate 2 is rotatable about an axis of the screw 11 within a predetermined range.

Figure 2:
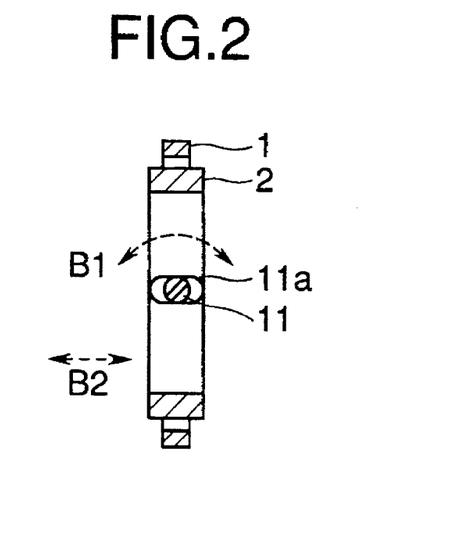
FIG. 2 is a sectional view taken along the line II—II of FIG. 1.

The holding plate 2 is further, as illustrated in a sectional view of FIG. 2 taken along the line II—II of FIG. 1, formed with a guide groove 11a assuming an elongate hole-like shape. The holding plate 2 is so constructed as to be movable in B2-directions in FIG. 2 within the predetermined range with respect to the spectacle frame 1. Note that B1 in FIG. 2 indicates rotating directions of the above holding plate 2. A screw head of the screw 11 is fitted in the guide groove 11a to a preferable extent enough to be possible of displacement by applying a predetermined force to the holding frame 20 for holding the aspherical inverted image lens 10 when mounting, as will be explained later, the aspherical inverted image lens 10 in the holding plate 2.

According to the thus constructed holding plate 2, the optical axis of the aspherical inverted image lens 10 secured via the holding frame 20 to the holding plate 2 can be adjusted to make a predetermined angle to the optical axis of an examined eye 15, and, besides, W.D can be also adjusted. Setting of W.D is adjusted before mounting the holding frame 20 to the holding plate 2.

When observing the fundus of eye, the aspherical inverted image lens 10 is rotated about the screw 11 in the up-and-down directions, thereby making it possible to easily eliminate unnecessary reflected light beams reflected by the surface of the aspherical inverted image lens 10. The examiner is therefore capable of observing the fundus of the examined eye in a more preferable state.

The examinee wears the auxiliary instrument in which the aspherical inverted image lens 10 is mounted through the holding frame 20 to the holding plate of the spectacle frame 1, whereby the optical axis of the aspherical inverted image lens 10 and the optical axis of the examined eye 15 are substantially fixed at the predetermined angle. Besides, the holding plate 2 is movable in the optical-axis direction of the aspherical inverted image lens 10 fixed to the holding plate 2. With this construction, W.D can be also micro-adjusted in accordance with a difference in the position of the fundus of the examined eye between the individuals.

Further, in accordance with this embodiment, the spectacle frame 1 has been exemplified as a member for mounted with the holding plates 2. The present invention is not, however, limited to the spectacle frame 1 for mounting the holding plates 2 but may be applied to, e.g., a Goggle type frame.

Figure 3:
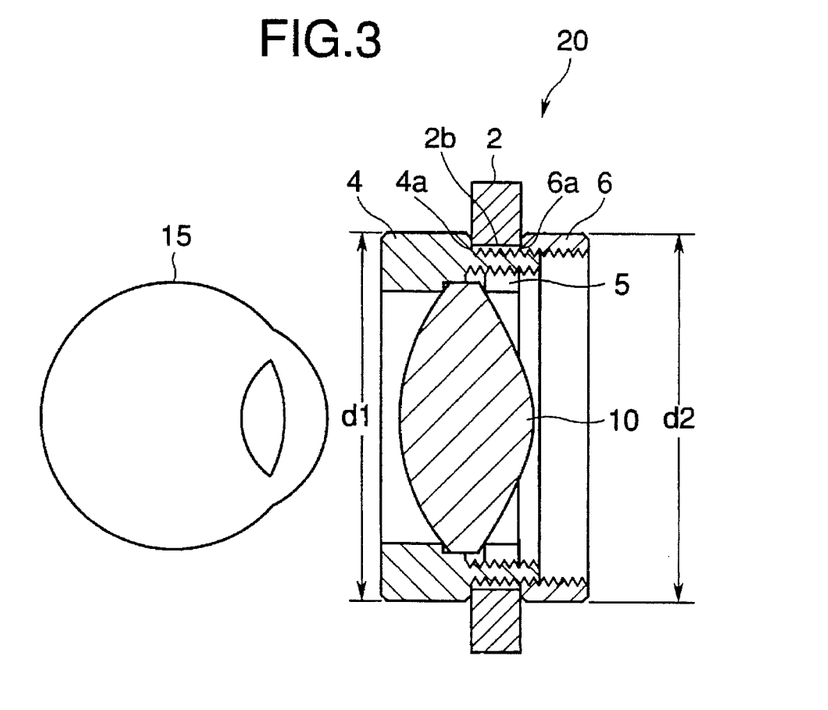
FIG. 3 is a sectional view illustrating a state where an aspherical inverted image lens is mounted in a holding frame.
Figure 4:
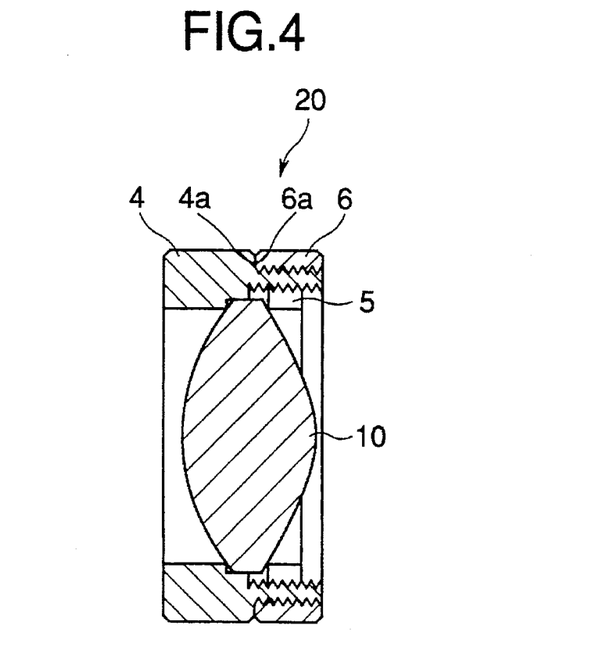
FIG. 4 is a sectional view showing a state where annular members constituting the holding frame of FIG. 3 are joined (used while holding it with a hand)

The holding frame 20 of the aspherical inverted image lens 10, as illustrated in FIGS. 3 and 4, includes an annular member 4 taking a cylindrical shape, a presser ring 5 for fixing the aspherical inverted image lens 10 inserted into the annular member 4 and an annular member 6 having a structure separable from and fittable to the annular member 4. A male thread is formed on an outer peripheral surface of this annular member 4, while a female thread engaging with the male thread of the annular member 4 is formed in an inner peripheral surface of the annular member 6. Note that the illustration of the spectacle frame 1 is omitted in FIG. 3.

In this embodiment, a major diameter of a portion, formed with the male thread, of the annular member 4 is set smaller than a minor diameter of an elongate hole 2a of the holding plate 2. Further, the annular members 4, 6 are so formed that a major diameter d1 of the annular member 4 and a major diameter d2 of the annular member 6 are substantially equalized but set smaller than the minor diameter of the elongate hole 2a.

Based on such a construction, when the annular members 4, 6 engage with each other, an inside peripheral portion 2b of the flame plate 2 is interposed between side surfaces 4a, 6a of the two annular members 4, 6, with the result that the aspherical inverted image lens 10 fixed to the annular member 4 can be fixed to the holding plate 2.

In this embodiment, it is assumed that the elongate hole 2a takes, as illustrated in FIG. 1, an elliptical shape formed when, e.g., a circle having a predetermined diameter moves a predetermined distance in a rectilinear direction and that the minor diameter of the elongate hole 2a indicates the diameter of the above circle. Accordingly, the mounting position of the holding frame 20 including the aspherical inverted image lens 10 to the holding frame 20 is freely changeable in the right-and-left directions or the up-and-down directions of the elongate hole 2a.

When mounting the aspherical inverted image lens 10 in the spectacle frame 1, the annular member 6 is separated from the annular member 4, and the male thread of the annular member 4 is inserted into the elongate hole 2a of the holding plate 2 mounted beforehand in the spectacle frame 1. Next, the annular member 6 is inserted from the opposite side of the holding plate 2, and a part 2b of the inside peripheral portion of the elongate hole 2a is interposed between the two annular members and thus fixed thereto.

Figure 5:
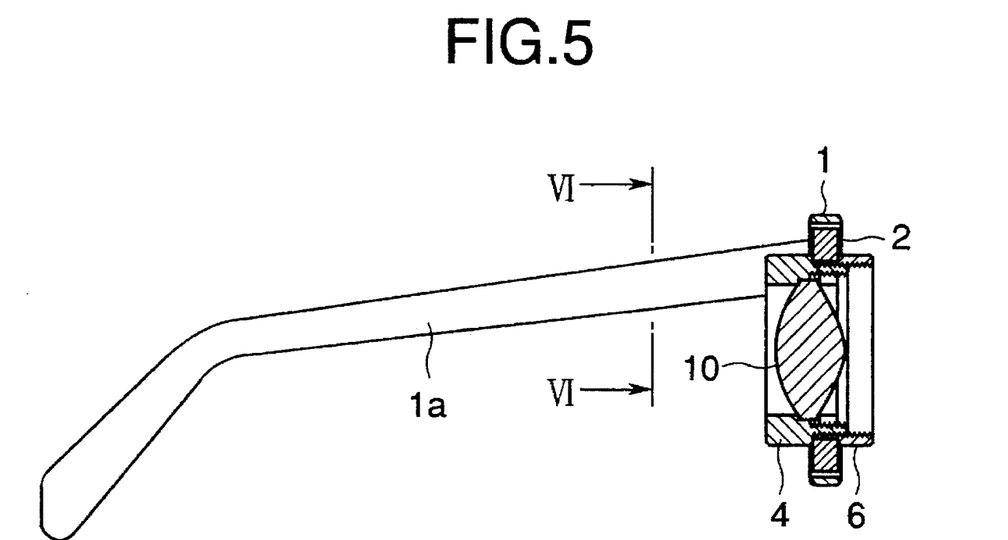
FIG. 5 is a sectional view illustrating a configuration of a whole frame in this embodiment.
Figure 6:
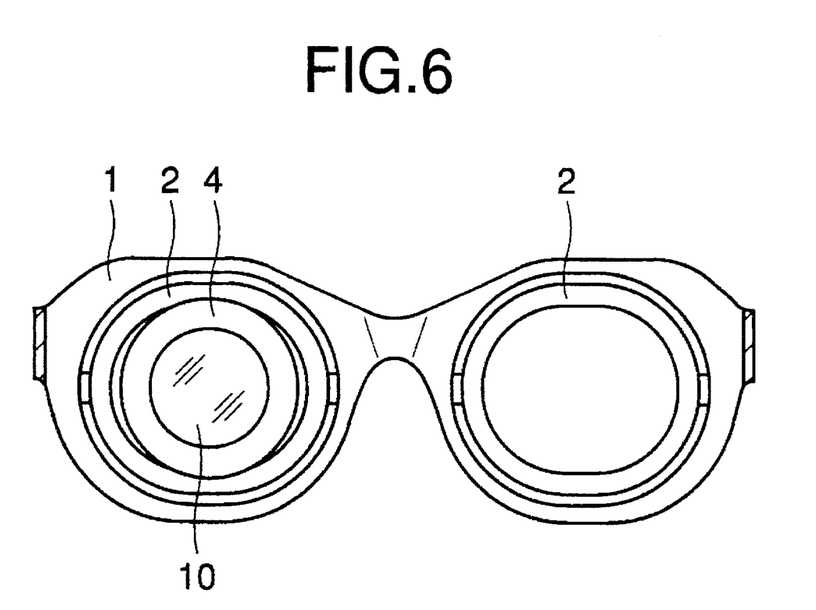
FIG. 6 is a sectional view taken along the line VI—VI of FIG. 5.

FIG. 5 illustrates a state where the fundus of eye observation auxiliary instrument in this embodiment is all assembled, and the aspherical inverted image lens 10 is mounted in the spectacle frame 1 through the above-described annular members 4, 6. Herein, FIG. 5 is a sectional view of the same auxiliary instrument as viewed from the side surface. Referring to FIG. 5, the symbol 1a indicates a temple portion of the spectacle frame 1, through which the examinee wears the spectacle frame 1. Further, FIG. 6 is a sectional view taken along the line VI—VI of FIG. 5. Note that FIG. 6 illustrates a state where one of the two holding plates 2 attached to the spectacle frame 1 is interposed therebetween, and the aspherical inverted image lens 10 is mounted therein.

Based on such a construction, the examiner slackens the annular member 6 and makes a micro-adjustment in the up-and-down and right-and-left directions so that the annular member 4 comes to the center of pupil of the examinee through the elongate hole 2a of the frame plate 2. Then, the examiner again fixes it with the annular member 6. The optical axis of the examinee can be thereby made coincident with the optical axis of the aspherical inverted image lens L.

The slit-lamp microscope 52 usable together with the fundus of eye observation auxiliary instrument described above may comprise, as illustrated in, e.g., FIG. 8, a chin sustainer rod 53 equipped with a chin sustainer 54, an illumination optical system 31 and an observation optical system 32. The illumination optical system 31 includes a halogen lamp 21, a slit stop 22 and a prism 23. The observation optical system 32 has a microscope unit 25 and an eyepiece element 26.

According to the fundus of eye observation system including the fundus of eye observation auxiliary instrument in this embodiment, the examiner is capable of readily observing an image of the fundus of the examined eye by making the optical axis of the slit-lamp microscope 52 coincident with the optical axis of the aspherical inverted image lens 10 in a state where the examinee wearing the spectacle frame 1 to which the aspherical inverted image lens 10 is fixed puts his chin on the chin sustainer 53.

Even if the face of the examinee slightly moves, W.D and the optical axis of the aspherical inverted image lens 10 with respect to the pupil of the examinee are fixed by the spectacle frame 1, and hence, when re-observing it, the optical axis of the slit-lamp microscope 52 may be readjusted. The image of the fundus of eye can be re-observed by a much simpler operation than the conventional operation.

Furthermore, the holding frame of the aspherical inverted image lens 10 takes the separable/fittable structure as done in the annular members 4, 6, and, therefore, the examiner is able to observe the image of the fundus of eye even when using the same method as the prior art by combining, as shown in FIG. 4, the annular member 4 with the annular member 6 in the case of the observing the image of the fundus of eye while holding the aspherical inverted image lens 10 with a hand.

Moreover, according to this embodiment, even when the face of the examinee moves, there is always kept a fixed distance between the examined eye 15 and the aspherical inverted image lens 10. Accordingly, there is no possibility in which the aspherical inverted image lens 10 mistakenly contacts the examined eye 15 enough to hurt the examined eye 15.

It is apparent that, in this invention, a wide range of different working modes can be formed based on the invention without deviating from the spirit and scope of the invention. This invention is not restricted by its specific working modes except being limited by the appended claims.

What is claimed is:

1. An auxiliary instrument for observing a fundus of eye, comprising:

an ophthalmic lens for forming an image of light beam reflected by the fundus of an examined eye;

a lens holding member for holding said ophthalmic lens;

a frame mounted with said lens holding member and put on the head or a part of the face of an examinee so that said ophthalmic lens is located in front of the examined eye of the examinee; and an inclination mechanism, provided between said lens holding member and said frame, for inclining an optical axis of said ophthalmic lens at a predetermined angle to an optical axis of the examined eye.

2. The auxiliary instrument according to claim 1, wherein said frame is a spectacle frame formed with an aperture in a face-to-face position with the examined eye of the examinee, and said lens holding member is held in the aperture of said spectacle frame.

3. The auxiliary instrument according to claim 1, further comprising a mechanism for moving said ophthalmic lens in directions of right and left eyes of examinee.

4. The auxiliary instrument according to claim 1, wherein said lens holding member is formed with elongate apertures extending in the directions of the right and left eyes of the examinee, and said ophthalmic lens is so held in the elongate aperture extending directions or directions orthogonal thereto.

5. The auxiliary instrument according to claim 4, wherein said lens holding member has:

a lens ring into which said ophthalmic lens is internally inserted;

an auxiliary ring detachably attached to said lens ring; and a frame plate mounted in said frame and interposed between said lens ring and said auxiliary ring, and wherein said ophthalmic lens is moved in the directions of the right and left eyes by changing the interposing position of said frame plate between said lens ring and said auxiliary ring.

6. The auxiliary instrument according to claim 1, wherein said ophthalmic lens is an aspherical inverted image lens.

7. The auxiliary instrument according to claim 1, further comprising a mechanism, provided between said lens holding member and said frame, for moving said ophthalmic lens in the optical-axis direction of the examined eye.

8. An auxiliary instrument for observing a fundus of eye, comprising:

an ophthalmic lens for forming an image of light beam reflected by the fundus of an examined eye;

a lens holding member for holding said ophthalmic lens; and a frame mounted with said lens holding member and put on the head or a part of the face of an examinee so that said ophthalmic lens is located in front of the examined eye of the examinee, wherein said lens holding member has at least one of a first moving mechanism for moving said ophthalmic lens in an optical-axis direction of the examined eye, a second moving mechanism for moving said ophthalmic lens in directions of the right and left eyes, and an inclination mechanism for inclining the optical axis of said ophthalmic lens to the optical axis of the examined eye.

9. An ophthalmic system comprising:

a microscope for irradiating an examined eye with slit light beam;

an ophthalmic lens for forming an image of the slit light beam on the examined eye; and a frame, for holding said ophthalmic lens, put on the head or a part of the face of the examinee so that said ophthalmic lens is located in front of the examined eye and having an inclination mechanism for inclining an optical axis of said ophthalmic lens to an optical axis of the examined eye, wherein said ophthalmic lens forms an image of reflected light beam reflected from the examined eye, and said microscope observes the reflected light beam the image of which is formed by said ophthalmic lens.

* * * * *